United States Patent [19]

Denton et al.

[11] 4,424,486
[45] Jan. 3, 1984

[54] PHASE ROTATION CIRCUIT FOR AN EDDY CURRENT TESTER

[75] Inventors: Clyde J. Denton, Bellevue; Lloyd T. Lamb, Issaquah, both of Wash.

[73] Assignee: Zetec, Inc., Issaquah, Wash.

[21] Appl. No.: 196,197

[22] Filed: Oct. 14, 1980

[51] Int. Cl.³ .................. G01N 27/72; G01R 33/12; H03L 7/00
[52] U.S. Cl. .................................. 324/225; 324/233; 328/155
[58] Field of Search ................... 324/202, 225, 233; 328/155

[56] References Cited

U.S. PATENT DOCUMENTS

| | | | |
|---|---|---|---|
| 3,358,225 | 12/1967 | Peugeot | 324/40 |
| 3,611,120 | 10/1971 | Forster | 324/37 |
| 3,848,182 | 11/1974 | Gerner et al. | 324/233 |
| 3,974,442 | 8/1976 | Savidge et al. | 324/37 |
| 4,084,136 | 4/1978 | Libby et al. | 324/238 |
| 4,095,469 | 6/1978 | Yamada et al. | 73/362 R |
| 4,215,310 | 7/1980 | Schwerer | 324/225 |

FOREIGN PATENT DOCUMENTS

| | | |
|---|---|---|
| 1130870 | 10/1968 | United Kingdom . |
| 1429620 | 3/1976 | United Kingdom . |
| 1481223 | 7/1977 | United Kingdom . |
| 1521203 | 8/1978 | United Kingdom . |

Primary Examiner—Gerard R. Strecker
Assistant Examiner—Walter E. Snow
Attorney, Agent, or Firm—Dowrey & Cross

[57] ABSTRACT

An Eddy Currest Tester for detecting defects in conductive materials employs phase rotation circuitry for eliminating the effects of lift-off signals from the reactive component of the output of an eddy current probe. An operator digitally selects a frequency which is input to the eddy current probe which is adjacent a test material. The signal output from the eddy current probe is amplified and demodulated into reactive and resistive components which are processed by phase rotation circuitry. The phase rotation circuitry is calibrated by applying a lift-off signal thereto while a phase adjust switch is on. When the phase adjust switch is on the reactive signal component is applied to a zero crossing detector which in conjunction with a flip flop controls the counting direction of an counter which addresses a sine-cosine table in a eraseable programable read only memory. The sign-cosine values are strobed into a latch which provides the sine-cosine information to multiplying circuits which multiply the reactive and resistive signal components output of the demodulator by the sine and cosine stored in the latch. The outputs of the multiplying circuit are input to a phase rotator which outputs signals which are rotated in the complex plane by the angle corresponding to the sine and cosine stored in the latch. While the phase adjust switch is on, the reactive component of the output of the phase rotator hunts about zero. When the phase adjust switch is off, the phase rotator rotates the phase of any signal input into the multiplying circuitry by the angle indicated by the last sine and cosine values strobed into the latch.

6 Claims, 3 Drawing Figures

PHASE ROTATION CIRCUIT FOR AN EDDY CURRENT TESTER

BACKGROUND OF THE INVENTION

1 Field of the Invention

This invention relates generally to a device for testing for defects in materials and particularly to a device which uses the complex impedance plane technique of eddy current testing to detect defects in metal structures.

2. Description of the Prior Art

It is known in the art that variations in conductivity and permeability of a material indicate the presence of structural defects such as cracks and corrosion. In most testing applications an oscillator applies a sinusoidal electrical signal across a reference coil and a test coil, with the test coil adjacent the material being tested so that the sinusoidal electrical signal in the test coil induces eddy currents in the material under test. The eddy currents produce a corresponding magnetic field which is out of phase with the magnetic field of the test coil; therefore, these fields tend to cancel one another, which reduces the test coil voltage. The test coil voltage is therefore a function of the magnitude of eddy current flow in the test piece.

The magnitude of eddy currents in the test piece, and thus the test coil voltage, depends upon the permeability and conductivity of the material being tested. In materials such as 300 series stainless steel and aluminum alloys, the conductivity is usually the only significant variable. Defects in such materials decrease the conductivity, which disrupts the eddy currents, causing the magnitude thereof to decrease. Therefore, the test coil voltage increases to indicate that the test coil is adjacent a defect.

In most testing applications, variations in the spacing between the probe and the material produce an undesirable signal component which significantly affects the accuracy and reliability of the eddy current test results. The undesired signal is known as probe spacing, probe motion, probe wobble, or lift-off. Hereinafter, the undesired signal is referred to as "lift-off".

One prior art device for compensating for lift-off variations requires an operator to read a meter and to manually adjust a potentiometer to minimize the lift-off over a given thickness range for the test material. To accomplish this manual calibration, the operator may need to perform several adjustments of the potentiometer to attain the proper setting therefor.

A second prior art device for compensating for lift-off signal variations in an eddy current tester uses a dual channel receiver which is responsive to signals from a test probe. A test probe forms the inductive part of a tuned oscillator circuit which is connected to the receiver. The varying magnetic field induced in the test sample produces eddy currents; and a defect in the test sample causes a change in the amplitude and frequency of the oscillator output. While both the amplitude and the frequency of the oscillator output depend on both the probe-surface spacing and surface defects, the prior art teaches that the amplitude variations are primarily dependent on probe-surface spacing, or lift-off, whereas the frequency variations are more dependent upon surface defects than upon the lift-off. This second prior art device includes summing and difference amplifiers which process the amplitude and frequency information to produce output signals which are indicative of defects and the lift-off.

Both of the prior art devices require continuous power inputs which render the prior art unsuitable for battery-powered operation.

Accordingly, there is a need in the art of nondestructive material testing for an eddy current tester which affords ease of calibration and which permits battery-powered operation so that the utility of the device does not depend upon the availability of power lines to supply electricity to the system.

SUMMARY OF THE INVENTION

The present invention overcomes the difficulties and inconveniences associated with prior art eddy current testers. An eddy current tester according to the present invention is a portable, variable frequency device which employs the complex impedance plane technique of eddy current testing. The frequency of the test signal is digitally selected with typical frequencies ranging from 100 Hz to 990 KHz with crystal-controlled accuracy and stability.

The present invention includes phase rotation circuitry which rotates the x-y coordinate system until the undesired signal, usually lift-off, has a vertical component of zero volts. The phase rotation circuitry includes an eraseable programmable read only memory, hereinafter Eprom, which contains sine-cosine values which are used to rotate the coordinate system according to well-known trigonometric equations. The Eprom receives power only during calibration of the phase rotation circuitry and supplies the appropriate sine-cosine digital signals to latches which store the sine-cosine signals for input to circuitry which performs the calculations for rotating the coordinates.

After the phase is properly adjusted, only signals indicative of defects have a vertical component, which is detected by a meter or other suitable means.

DESCRIPTION OF THE PREFERRED EMBODIMENT

Figure 1:
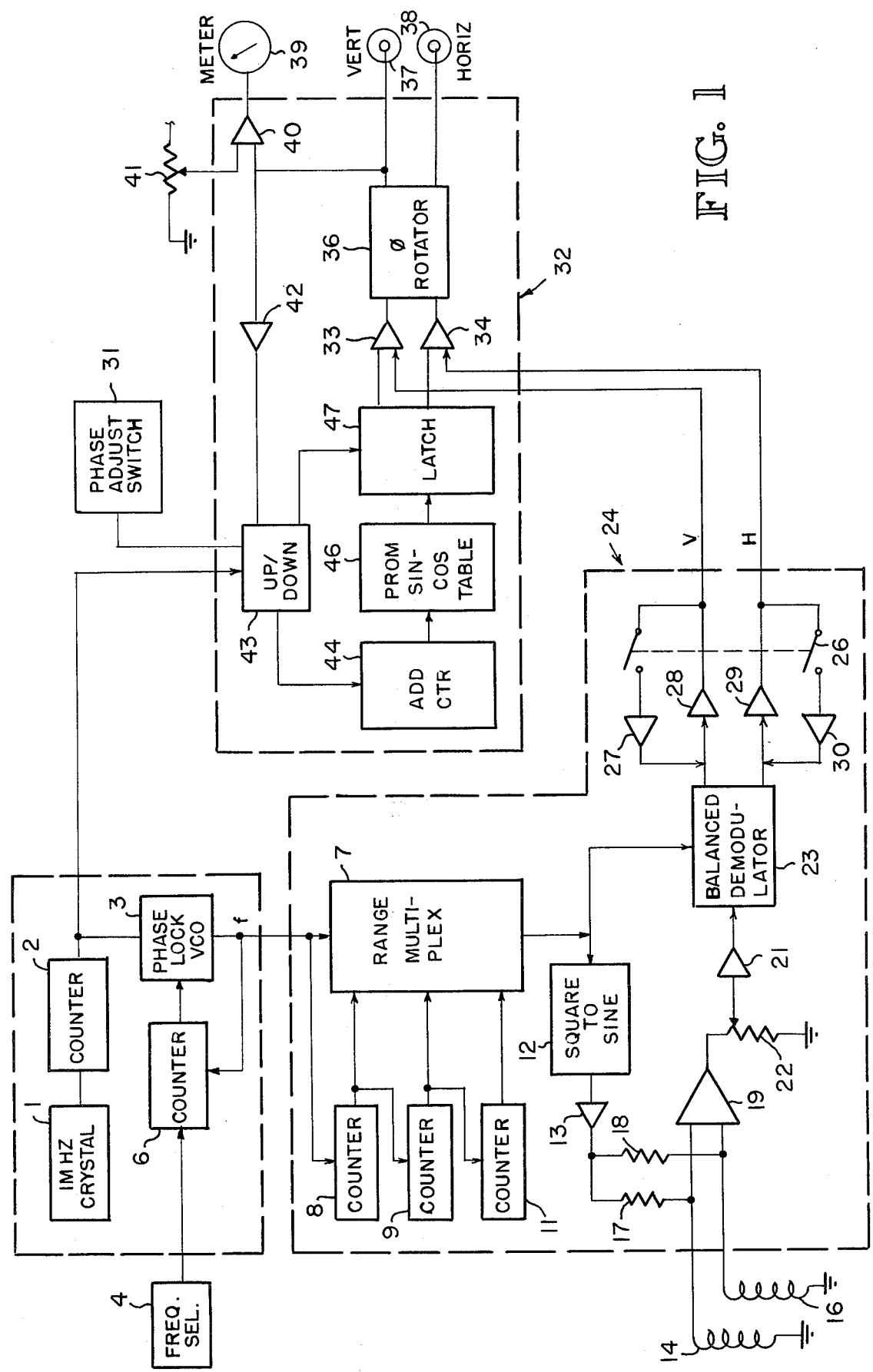
FIG. 1 is a block diagram of the invention.

Referring to FIG. 1, a 1 MHz crystal 1 supplies a square wave signal to a counter 2 which divides the frequency by 100 to provide a 10 KHz signal to a phase lock voltage controlled oscillator 3. A digital frequency selector 4 provides an input signal f to a second counter 6 which divides f by an integer N such that f/N = 10 KHz. The voltage controlled oscillator 3 outputs a signal having a frequency f = N·10 KHz to a range multiplex circuit 7 and to a third counter 8.

The counter 8 divides f by 10 and has outputs connected to the range multiplex circuit 7 and to a fourth counter 9. The counter 9 similarly divides the input frequency thereto by 10 and has outputs connected to the range multiplex circuit 7 and to a fifth counter 11 which divides the frequency input thereto by 10 and provides an output to the range multiplex circuit 7. Therefore, the range multiplex circuit permits the selection of test frequencies of f, 0.1 f, 0.01 f, and 0.001 f.

The square wave output of the range select multiplex circuit is connected to a square-to-sine conversion circuit 12 which provides a sine wave output to a power amplifier 13 which drives a reference probe 14 and a test probe 16 through resistances 17 and 18, respectively, which provide short circuit protection to the power amplifier 13. The reference probe 14 and the test probe 16 are preferably matched dual coil probes which are commercially available.

The outputs of the reference probe 14 and the test probe 16 are connected to a differential amplifier 19 with the output thereof being connected to an amplifier 21 through a gain control potentiometer 22. The output of the amplifier 21 and an output of the range multiplex circuit 7 are connected to a balanced demodulator 23. The balanced demodulator 23 converts the input signal thereto, which is a sine wave at the test frequency, into two dc signals V and H which correspond to the reactive and resistive components in the phasor representation of the sine wave signal from the amplifier 21. Since the output of the differential amplifier is proportional to the difference of the outputs of the reference probe 14 and the test probe 16, the signals V and H represent the differences of the corresponding components of the reference and test coil phasors.

The V and H signals from the balanced demodulator 23 are connected to a dc balance circuit 24 which comprises a balance switch 26 and amplifiers 27–30. The signals V and H should be balanced to zero in the complex plane under quiescent conditions. Closing the balance switch 26 to complete the loop comprising the amplifier 27 and the amplifier 28 for the V signal and the loop comprising the amplifier 29 and the amplifier 30 for the H signal provides the necessary offset to balance the signals to the origin in the complex plane.

After the instrument is balanced, a lift-off signal is deliberately introduced by varying the spacing between the coil and a standard piece with a nonconductive shim. Turning on a phase adjust switch 31 causes the lift-off signal to be processed by the phase rotation circuitry 32 to rotate the coordinate system until the vertical component of the lift-off signal is equal to zero. When the shim is removed and the test probe is placed in contact with the standard piece, the eddy current signal returns to the origin of the complex plane. After the phase has been adjusted, the eddy current tester is ready for operation.

The signals V and H from the probes 14 and 16 are input into multiplying digital-to-analog converters 33 and 34, respectively, which supply outputs to a phase rotator 36. The phase rotator 36 processes the input signals to rotate the coordinates according to the equations $$V_{out} = V \cos\theta - H \sin\theta$$

$$H_{out} = H \cos\theta + V \sin\theta,$$

which are the equations for rotating the X–Y coordinates system by the angle $\theta$. The phase rotator 36 has a vertical output 37 and a horizontal output 38 for connection to suitable display means. The vertical output of the phase rotator 36 is also input into an amplifier U1B which drives a meter 39. A potentiometer 41 provides means for adjusting the gain of the amplifier U1B. The vertical output of the phase rotator 36 is also connected to a zero detector circuit 42 which has the output thereof connected to an up/down counter 43. The up/down counter 43 also receives the 10 KHz reference signal from the counter 2 and an input from the phase adjust switch 31. The up/down counter 43 is connected to a binary counter 44 to control the counting direction thereof. The output of the binary counter 44 is connected to an Eprom 46, which is a 1024×8 erasable programmable read only memory. One-half of the memory locations contain an 8-bit-cosine weighting value look-up table, and the other half of the memory locations contain an 8-bit-sine weighting value look-up table. The Eprom is normally unpowered and is actuated only when the phase adjust switch 31 is on, which permits an eddy current tester according to the invention to be battery powered or line powered. The output of the Eprom 46 is connected to a latch circuit 47 which also receives an input from the up/down counter 43. The latch 47 supplies outputs to the multiplying digital-to-analog converters 33 and 34, which provide differential current outputs to the phase rotator 36.

If the output of the zero detector 42 is positive when the phase adjust switch is turned on, then the up/down counter 43 causes the binary counter 44 to count down until the vertical output reaches zero or until the phase adjust switch is turned off, which disconnects power from the up/down counter 43, the binary counter 44 and the Eprom 46. As the binary counter 44 counts, the 8-bit words which represent the sine and cosine values are addressed in succession and edge clocked into the strobe latch 44 at appropriate timing sequences. The latch 47 retains the sine and cosine values and supplies digital signals indicative thereof to the multiplying digital-to-analog converters 33 and 34. The phase rotator 36 processes the outputs of the multiplying digital-to-analog converters 33 and 34 to rotate the coordinates according to the above-stated equation.

If the phase adjust switch 31 is on, and the output of the zero detector 42 is positive, the binary counter 44 continues to count down; and the Eprom supplies another set of sine-cosine values into the latch 47. The coordinates rotate until the output of the zero detector 42 is negative, which causes the up/down counter 43 to command the binary counter 44 to count up, which causes the coordinates to rotate in the direction opposite to the previous direction of rotation until the output of the zero detector 42 again changes states. The system hunts back and forth across the horizontal axis until the phase adjust switch 31 is turned off, at which time the latch 47 retains the last sine-cosine information supplied thereto. After the phase adjust switch 31 is turned off, any phasor signal indicated by the components V and H from the probes 14 and 16 will be rotated by the phase rotator 36 through the angle $\theta$ indicated by the sines and cosines which are stored in the latch 47.

After the phase has been adjusted, any lift-off signal will have only a horizontal component, and defects, such as cracks and corrosion, in a test sample will result in a signal which has a vertical component which may be easily read on the meter 39 or connected to other suitable display means.

Figure 2A:
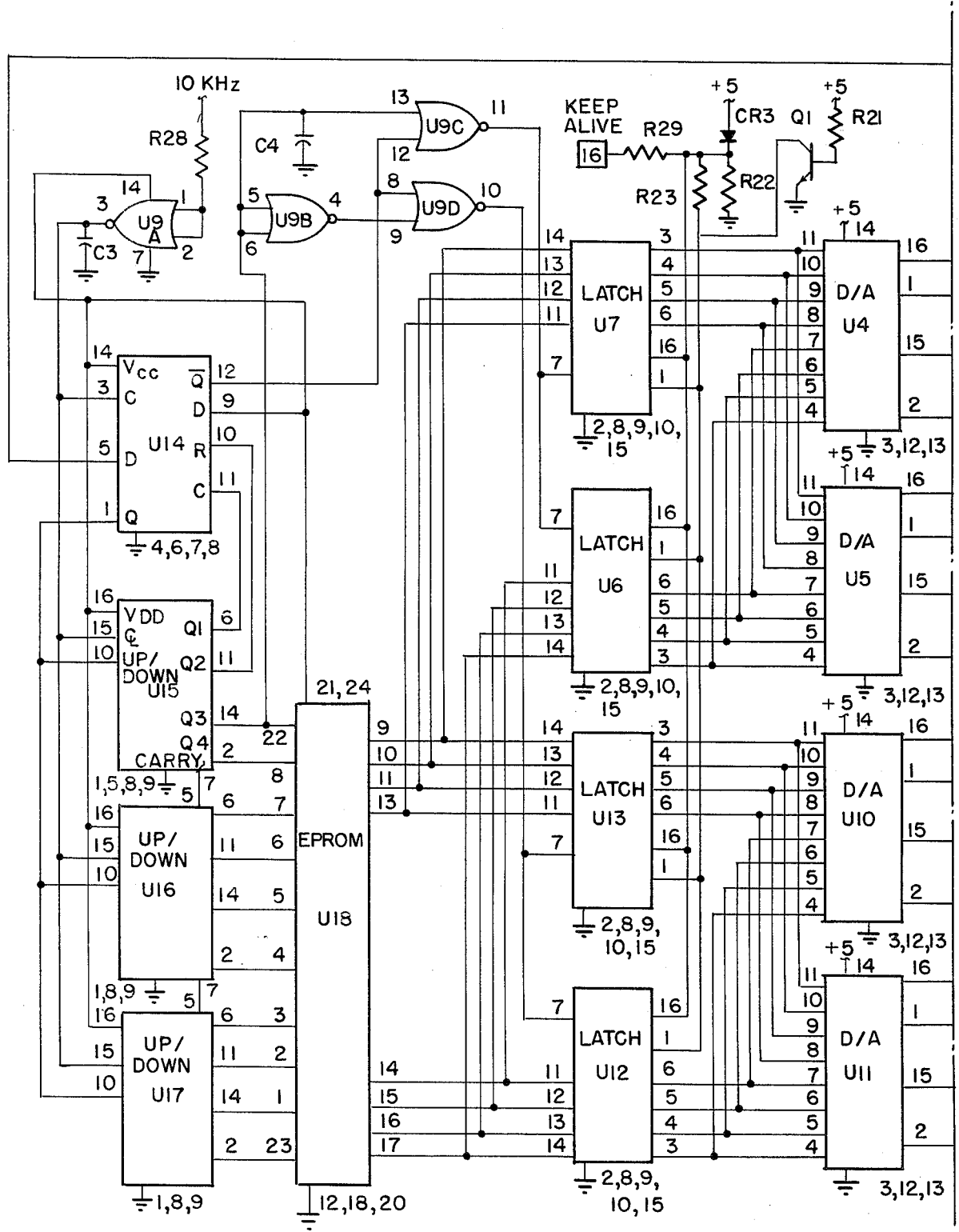
FIGS. 2A and 2B comprise a schematic of the coordinate rotation circuitry of FIG. 1.
Figure 2B:
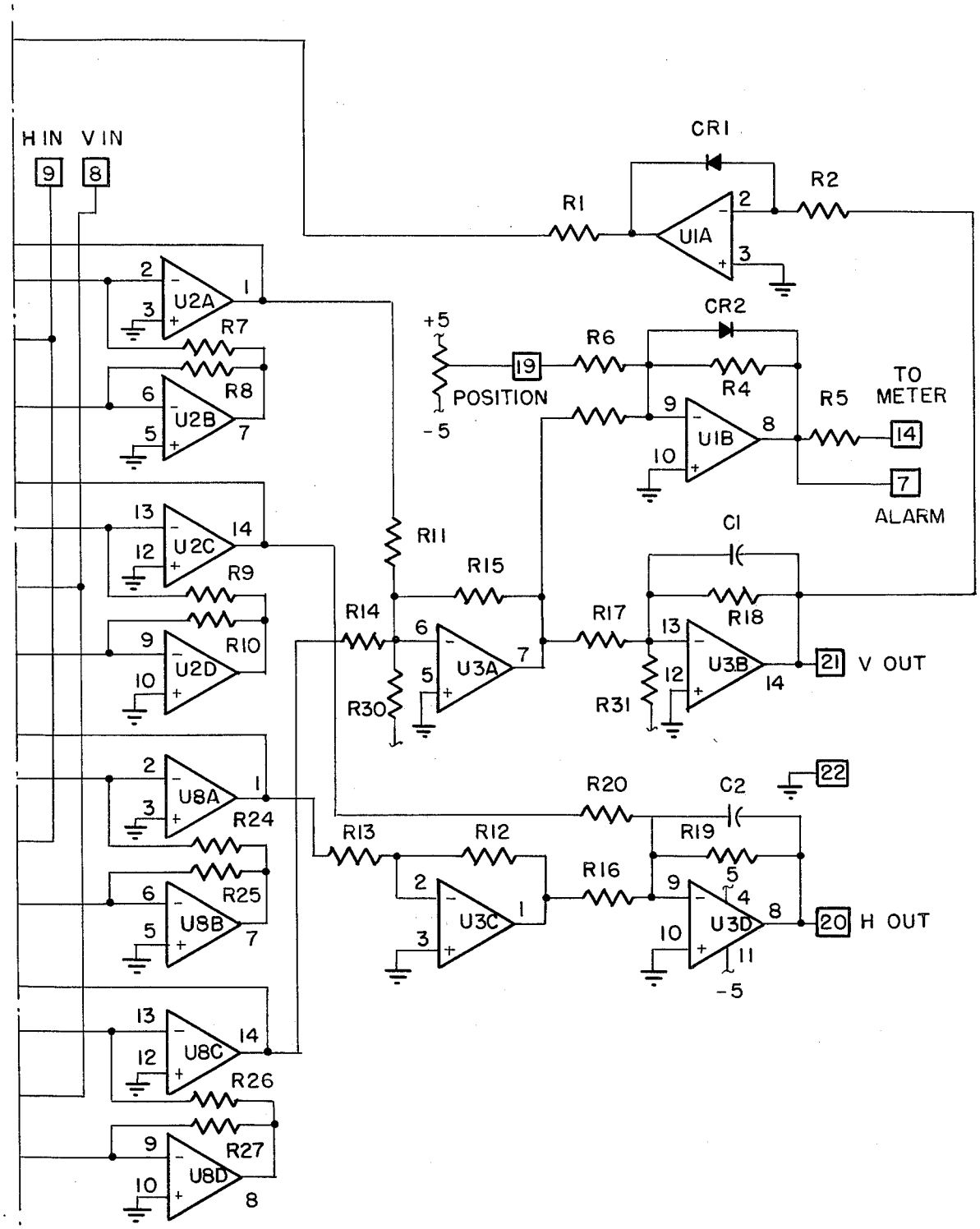

Referring to FIGS. 2A and 2B, the signal V is input into a first digital-to-analog converter U5 at pin 15 and to a second digital-to-analog converter U11 also at pin 15; and the signal H is input to pin 15 of a digital-to-analog converter U4 and to a second digital-to-analog converter U10. The digital-to-analog converters U4 and U5 receive inputs indicative of the sine of the angle of coordinate rotation from each of a pair of strobe latches U6 and U7; and similarly the digital-to-analog converters U10 and U11 each receive inputs indicative of the negative of the cosine of the angle from a pair of strobe latches U12 and U13. The digital-to-analog converter U4 has outputs 1 and 2 connected to the negative input terminals of an operational amplifier U2A and an operational amplifier U2B, respectively. The positive inputs of the operational amplifiers U2A and U2B are grounded and a resistance R7 is connected between the negative input of the operational amplifier U2A and the output of U2B. A resistance R8 is connected between the output and the negative input of U2B. The operational amplifiers U2A and U2B and the resistances R7 and R8 comprise a multiplying circuit which produces an output at pin 1 of U2A which is proportional to the product of the signals input to the operational amplifiers U2A and U2B. The inputs to U2A and U2B are H and sin $\theta$ respectively; and in addition to multiplying the inputs, the operational amplifiers perform a sign change so that the output at pin 1 of the operational amplifier U2A is $-H \sin \theta$. Similarly, the operational amplifiers U2C and U2D with associated resistances R9 and R10; the operational amplifiers U8A and U8B with associated resistance R24 and R25; and the operational amplifiers U8C and U8D with associated resistances R26 and R27 each comprise additional multiplying circuits similar to the multiplying circuit hereinabove described. Since the signal V is supplied to pin 15 of the digital-to-analog converter U5, the output at pin 14 of U2C equals $-V \sin \theta$, while the output at pin 1 of U8A is $+H \cos \theta$ and the output at pin 14 of U8C is $+V \cos \theta$.

The output at pin 14 of U8C is connected to a summing inverter which comprises an operational amplifier U3A and resistances R11, R14, R15 and R30. The output at pin 7 of the operational amplifier U3A is input into an inverter which comprises an operational amplifier U3B, resistances R17, R18 and R31, and capacitor C1. The output at pin 14 of the operational amplifier U3B is $V_{out} = V \cos \theta - H \sin \theta$. The output H cos $\theta$ from pin 1 of the operational amplifier U8A is connected to an inverter which comprises an operational amplifier U3C and resistances R12 and R13; and the output of the operational amplifier U3C and the output from pin 14 of the operational amplifier U2C are connected to a summing inverter comprising an operational amplifier U3D, a capacitor C2 and resistances R16, R19 and R20. The output of U3D is therefore $$H_{out} = H \cos \theta + V \sin \theta.$$

The output of U3A, which is $$-V_{out} = -V \cos \theta + H \sin \theta$$

is input to an inverter which comprises an operational amplifier U1B, a diode CR2 and resistances R3 and R4. The diode CR2 prevents the output at pin 8 of the operational amplifier U1B from going negative, thereby preventing reverse current through the movement of the meter 39, shown in FIG. 1, which is driven by the operational amplifier U1B through a resistance R5.

The output $V_{out}$ from pin 14 of the operational amplifier U3B is input into a comparator which comprises a resistance R2 connected to the negative input terminal off an operational amplifier and U1A to the anode of a diode CR1, which has the cathode thereof connected to the output of the operational amplifier U1A. The diode CR1 prevents the output of the operational amplifier U1A from going negative. The logic of the system is designed such that zero is one logic level and +5 is the other logic level; therefore a negative output from the operational amplifier U1A is undesirable.

The output of the comparator is connected through a resistance R1 to the data input of a dual type D flip-flop U14. The C and Q terminals of the flip-flop U14 are connected to the inputs of decade binary counters U15, U16 and U17. The operational amplifier U1A and the flip-flop U14 cooperate to function as a steering latch to control the counting direction of the decade binary counters U15–U17. If the output of U1A indicates that the input thereto is positive, then the flip-flop U14 will cause the counters U15–U17 to count down. The numbers which the counters U15–U17 count correspond to sine and cosine values stored in an erasable programmable read only memory U18, hereinafter referred to as Eprom U18. The Eprom U18 stores 512 sine values and 512 cosine values, so that the angle corresponding to successive addresses within the Eprom U18 is $2\pi/512$. The 10 KHz reference signal is used as a clock and is applied to the clock inputs of the flip-flop U14 and the counters U15–U17 through a NOR gate U9A and a resistance R28. As the count ripples through pin 14 of the counter U15, a strobe pulse is generated by the $\overline{Q}$ output of the flip-flop U14 and a plurality of NOR gates U9B, U9C and U9D between address changes in the Eprom U18. This strobe pulse transfers the sine table number from the Eprom U18 into the latches U6 and U7 and strobes the negative of the cosine numbers into the latches U12 and U13.

The latches U6, U7, U12 and U13 supply signals to the digital-to-analog converters U4, U5, U10 and U11 as previously described. The counters U15–U17 count down and address successive locations in the Eprom U18 to cause the outputs of the digital-to-analog converters to step through a sequence of values and to rotate the coordinate system to reduce the signal input into the operational amplifier U1A. If the signal $V_{out}$ goes negative, the output of the operational amplifier U1A will be zero; and the flip-flop U14 will cause the counters U15–U17 to count up to address sine and cosine values in the Eprom U18 to again move the vertical component toward zero. The output at pin 14 of the operational amplifier U3B hunts about zero as long as the phase adjust switch 31 of FIG. A1 is on.

When the phase adjust switch 31 is turned off, a diode CR3 connected between a suitable power supply such as a five volt power supply (not shown) provides voltage to pin 16 of the latches U6, U7, U12 and U13. The voltage to the $V_{DD}$ terminals of the latches goes from regulated +5 volts to approximately 4 volts DC, which keeps the sine-cosine information in the latches when the phase adjust switch is turned off. A resistance R21 is connected between the 5 volt power supply and the base of a transistor Q1 which has a grounded emitter and which has the collector connected to pin 1, the disable input, of the latches. When the instrument power is turned off, the transistor Q1 shuts off, which pulls the disable input of the latches up, thereby putting the latch outputs in high impedance states to prevent the latch outputs from supplying current to other circuits. A keep-alive terminal 16 is connected to the power source to provide power to the latches at all times.

Although the present invention has been described with reference to a particular embodiment thereof, it will be understood by those skilled in the art that numerous modifications may be made without departing from the scope of the invention. Accordingly, all modifications and equivalents which are properly within the scope of the appended claims are included in the present invention.

What is claimed is:

1. A phase rotation circuit, comprising:
signal means for providing a calibration signal and a test signal, said calibration signal having a reactive calibration signal component and a resistive calibration signal component, said test signal having a reactive test signal component and a resistive test signal component;
means for determining the sine and cosine of the phase angle determined by said reactive calibration signal component and said resistive calibration signal component;
means for storing the sine and cosine of said phase angle;
first multiplying means connected to said storing means for forming the product of the sine and cosine of said phase angle and said reactive test signal component;
second multiplying means connected to said storing means for forming the product of the sine and cosine of said phase angle and said resistive test signal component; and
phase rotator means for combining said products to produce a phase rotator output rotated by said phase angle from said test signal such that said phase rotator has a reactive phase rotator output component equal to the difference of said reactive test signal component and said reactive calibration signal component, said determining means including a zero crossing detector for detecting zero crossings of said reactive component of said phase rotator output, said zero crossing detector producing a logic output indicative of the sign of the signal input thereto.

2. A phase rotation circuit, comprising:
signal means for providing a calibration signal and a test signal, said calibration signal having a reactive calibration signal component and a resistive calibration signal component, said test signal having a reactive test signal component and a resistive test signal component;
means for determining the sine and cosine of the phase angle determined by said reactive calibration signal component and said resistive calibration signal component;
means for storing the sine and cosine of said phase angle;
first multiplying means connected to said storing means for forming the product of the sine and cosine of said phase angle and said reactive test signal component;
second multiplying means connected to said storing means for forming the product of the sine and cosine of said phase angle and said resistive test signal component; and
phase rotator means for combining said products to produce a phase rotator output rotated by said phase angle from said test signal such that said phase rotator has a reactive phase rotator output component equal to the difference of said reactive test signal component and said reactive calibration signal component, said determining means including a zero crossing detector for detecting zero crossings of said reactive component of said phase rotator output, said zero crossing detector producing a logic output indicative of the sign of the signal input thereto and means responsive to the output of said zero crossing detector for selectively causing said reactive phase rotator output to reach zero.

3. A phase rotation circuit according to claim 2 including counting means having the counting direction thereof responsive to the output of said zero crossing detector;
a read only memory connected to said counting means, said read only memory having a table of sines of angles and a table of cosines of angles stored therein with the sine and cosine of an angle being selectively addressable by said counting means;
a latch connected to said read only memory, said latch comprising means for storing signals indicative of the sine and cosine of an angle therein; and
means for sequentially transferring signals indicative of the sines and cosines of angles from said read only memory to said latch, whereby said latch outputs signals indicative of the sine and cosine of a selected angle to said first and second multiplying means.

4. A phase rotation circuit according to claim 3, further including:
means for supplying electrical power to said read only memory and said counting means; and
means for selectively disconnecting said means for supplying power from said read only memory and said counting means to supply electrical energy thereto only during calibration of said phase rotation circuit.

5. A phase rotation circuit, comprising:
signal means for providing a calibration signal and a test signal, said calibration signal having a reactive calibration signal component and a resistive calibration signal component, said test signal having a reactive test signal component and a resistive test signal component;
means for determining the sine and cosine of the phase angle determined by said reactive calibration signal component and said resistive calibration signal component, said determining means including normally unpowered memory means for storing a table of sine and cosine values;
means for selectively supplying power to said memory means;
means for storing the sine and cosine of said phase angle;
first multiplying means connected to said storing means for forming the product of the sine and cosine of said phase angle and said reactive test signal component;
second multiplying means connected to said storing means for forming the product of the sine and cosine of said phase angle and said resistive test signal component; and
phase rotator means for combining said products to produce a phase rotator output rotated by said phase angle from said test signal such that said phase rotator has a reactive phase rotator output component equal to the difference of said reactive test signal component and said reactive calibration signal component.

6. A phase rotation circuit comprising:
means for providing a calibration signal and a test signal;
means for determining the sine and cosine of the phase angle of said calibration signal including normally unpowered memory means for storing a table of sine and cosine values, and means for selectively supplying power to said memory means;
multiplying means for forming the products of said sine and cosine and the resistive and reactive components of said test signal; and
phase rotator means for combining said products to produce a phase rotator output rotated by the phase angle from said test signal such that said phase rotator has a reactive phase rotator output component equal to the difference of said reactive test signal component and said reactive calibration signal component.

* * * * *